United States Patent
Dogra et al.

(10) Patent No.: US 11,766,484 B2
(45) Date of Patent: Sep. 26, 2023

(54) EXOSOME VESSELS FOR DELIVERY OF MOLECULAR CARGO

(71) Applicant: International Business Machines Corporation, Armonk, NY (US)

(72) Inventors: Navneet Dogra, New York City, NY (US); Gustavo Alejandro Stolovitzky, Riverdale, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 286 days.

(21) Appl. No.: 16/239,052

(22) Filed: Jan. 3, 2019

(65) Prior Publication Data

US 2020/0215201 A1 Jul. 9, 2020

(51) Int. Cl.
*A61K 47/69* (2017.01)

(52) U.S. Cl.
CPC ................................ *A61K 47/6901* (2017.08)

(58) Field of Classification Search
CPC ................ A61K 35/00; A61K 47/6903; A61K 47/6901; A61K 47/60; A61K 47/59; A61K 47/56; A61K 47/549; C12N 2310/16; C12N 2320/32; C12N 15/111; C08L 33/26
See application file for complete search history.

(56) References Cited

U.S. PATENT DOCUMENTS

| | | |
|---|---|---|
| 16,027,726 | 2/2000 | Ansell |
| 9,085,778 B2 | 7/2015 | Lotvall et al. |
| 2012/0093885 A1 | 4/2012 | Sahoo et al. |
| 2016/0024503 A1 | 1/2016 | Kalluri et al. |
| 2017/0059572 A1 | 3/2017 | Kalluri et al. |
| 2018/0015182 A1 | 1/2018 | Lu et al. |
| 2018/0067121 A1 | 3/2018 | Naasani |
| 2020/0215201 A1 | 7/2020 | Dogra et al. |
| 2020/0405640 A1 * | 12/2020 | Zhang ................ C07K 16/2809 |

FOREIGN PATENT DOCUMENTS

| | | | |
|---|---|---|---|
| CN | 105452466 A | 3/2016 | |
| CN | 107022516 A | 8/2017 | |
| CN | 109082404 A | 12/2018 | |
| WO | WO-2014068408 A2 * | 5/2014 | ................ A61P 9/12 |
| WO | 2017124000 A1 | 7/2017 | |
| WO | 2017/173034 A1 | 10/2017 | |
| WO | 2017176894 A1 | 10/2017 | |
| WO | WO-2017176894 A1 * | 10/2017 | ........... A61K 9/1273 |
| WO | 2017194499 A1 | 11/2017 | |
| WO | 2018/046879 A1 | 3/2018 | |
| WO | 2018062973 A1 | 4/2018 | |

OTHER PUBLICATIONS

Lai CP, Mardini O, Ericsson M, Prabhakar S, Maguire CA, Chen JW, Tannous BA, Breakefield XO. Dynamic biodistribution of extracellular vesicles in vivo using a multimodal imaging reporter. ACS nano. Jan. 28, 2014;8(1):483-94. (Year: 2014).*
Gao X, Ran N, Dong X, Zuo B, Yang R, Zhou Q, Moulton HM, Seow Y, Yin H. Anchor peptide captures, targets, and loads exosomes of diverse origins for diagnostics and therapy. Science translational medicine. Jun. 6, 2018;10(444). (Year: 2018).*
Bunge A, Loew M, Pescador P, Arbuzova A, Brodersen N, Kang J, Dähne L, Liebscher J, Herrmann A, Stengel G, Huster D. Lipid membranes carrying lipophilic cholesterol-based oligonucleotides-characterization and application on layer-by-layer coated particles. J Phys Chem B. Dec. 24, 2009;113(51):16425-34. (Year: 2009).*
Raouane M, Desmaële D, Urbinati G, Massaad-Massade L, Couvreur P. Lipid conjugated oligonucleotides: a useful strategy for delivery. Bioconjugate chemistry. Jun. 20, 2012;23(6):1091-104. (Year: 2012).*
Chen T, Hedman L, Mattila PS, Jartti L, Jartti T, Ruuskanen O, Söderlund-Venermo M, Hedman K. Biotin IgM antibodies in human blood: a previously unknown factor eliciting false results in biotinylation-based immunoassays. PloS one. Aug. 3, 2012;7(8):e42376. (Year: 2012).*
Avidin-Biotin Technical Handbook. Thermo Fisher Scientific Inc. 2009. (Year: 2009).*
WordNet definition of "molecule" retrieved from onelook.com; Apr. 16, 2021 (Year: 2021).*
Wang R, Lu D, Bai H, Jin C, Yan G, Ye M, Qiu L, Chang R, Cui C, Liang H, Tan W. Using modified aptamers for site specific protein-aptamer conjugations. Chemical science. 2016;7(3):2157-61. (Year: 2016).*
Cui C, Zhang H, Wang R, Cansiz S, Pan X, Wan S, Hou W, Li L, Chen M, Liu Y, Chen X. Recognition-then-Reaction Enables Site-Selective Bioconjugation to Proteins on Live-Cell Surfaces. Angewandte Chemie. Sep. 18, 2017;129(39):12116-9. (Year: 2017).*
Wan S, Zhang L, Wang S, Liu Y, Wu C, Cui C, Sun H, Shi M, Jiang Y, Li L, Qiu L. Molecular recognition-based DNA nanoassemblies on the surfaces of nanosized exosomes. Journal of the American Chemical Society. Apr. 19, 2017;139(15):5289-92. (Year: 2017).*
Gao X, Ran N, Dong X, Zuo B, Yang R, et al. Anchor peptide captures, targets, and loads exosomes of diverse origins for diagnostics and therapy. Science Translational Medicine. Jun. 6, 2018;10(444). Cited in previous action. (Year: 2018).*
Riaz MK, Riaz MA, Zhang X, Lin C, Wong KH, Chen X, Zhang G, Lu A, Yang Z. Surface functionalization and targeting strategies of liposomes in solid tumor therapy: A review. International journal of molecular sciences. Jan. 2018;19(1):195. (Year: 2018).*
Friedman AD, E Claypool S, Liu R. The smart targeting of nanoparticles. Current pharmaceutical design. Oct. 1, 2013;19(35):6315-29. (Year: 2013).*

(Continued)

*Primary Examiner* — Robert M Kelly
(74) *Attorney, Agent, or Firm* — Amin, Turocy & Watson, LLP

(57) ABSTRACT

Techniques regarding the transportation and/or delivery of molecular cargo by exosomes are provided. For example, one or more embodiments described herein can comprise a molecule, which can comprise a chemically modified molecular cargo bonded to a surface biomolecule of an exosome. The surface biomolecule can be located on a bilayer membrane of the exosome opposite a cytoplasm of the exosome.

9 Claims, 12 Drawing Sheets

(56) References Cited

OTHER PUBLICATIONS

Molino NM, Anderson AK, Nelson EL, Wang SW. Biomimetic protein nanoparticles facilitate enhanced dendritic cell activation and cross-presentation. ACS nano. Nov. 26, 2013;7(11):9743-52. (Year: 2013).*
International Search Report and Written Opinion received for PCT Application Serial No. PCT/IB2019/ 060349 dated Mar. 17, 2020, 9 pages.
Gao et al., "Anchor peptide captures, targets, and loads exosomes of diverse origins for diagnostics and therapy" http://stm.sciencemag.org/, Jun. 6, 2018, 15 pages.
Purushothaman et al., "Fibronectin on the surface of myeloma cell-derived exosomes mediates exosome-cell interactions", http://www.jbc.org, Dec. 21, 2015, 24 pages.
Dykes., "Exosomes in Cardiovascular Medicine", http://www.medengine.com/Redeem/4028F06050164A0E, May 19, 2017, 13 pages.
Examination Report received for GB patent Application Serial No. 2110435.1 dated Jul. 18, 2022, 4 pages.
First Office Action received for Chinese Patent Application Serial No. 201980081714.0 dated Jul. 21, 2022, 18 pages (Including English Translation).
Office Action received for Chinese Patent Application Serial No. 201980081714.0 dated Dec. 5, 2022, 6 pages (Original Copy only).
Antimisiaris, et al., "Exosomes and exosome-inspired vesicles for targeted drug delivery," Pharmaceutics, 2018, 10. Jg., No. 4, p. 218, Published online Nov. 6, 2018. doi: 10.3390/pharmaceutics10040218.
Tian, et al., "A doxorubicin delivery platform using engineered natural membrane vesicle exosomes for targeted tumor therapy," Biomaterials, 2014, 35. Jg., No. 7, p. 2383-2390, doi: 10.1016/j.biomaterials.2013.11.083. Electronic publication date: Dec. 15, 2013.
DE Office Action for DE Application No. 11 2019 005 512.7 dated Feb. 22, 2023.
Notice of Reasons for Refusal received for Japanese Patent Application Serial No. 2021-526215 dated Jun. 28, 2023, 8 pages.
Wang, Andrew Z., et al. "Nanoparticle Delivery of Cancer Drugs." Annu. Rev. Med. 2012. 63:185-98. 17 pages.
Rosi, Nathaniel L., et al. "Oligonucleotide-Modified Gold Nanoparticles for Intracellular Gene Regulation." Science, vol. 312, May 19, 2006. 5 pages.
Sperling, Ralph A., et al. "Biological applications of gold nanoparticles." Chem. Soc. Rev., 2008, 37, 1896-1908. 15 pages.
Dogra, Navneet, et al. "Investigating ligand-receptor interactions at bilayer surface using electronic absorption spectroscopy and fluorescence resonance energy transfer." Langmuir. Sep. 11, 2012; 28(36): 12989-12998. 19 pages.
Dogra, Navneet, et al. "Micro-motors: A motile bacteria based system for liposome cargo transport." Scientific Reports, Jul. 5, 2016. 9 pages.
Valadi, Hadi, et al. "Exosome-mediated transfer of mRNAs and microRNAs is a novel mechanism of genetic exchange between cells." Nature Cell Biology, vol. 9, No. 6, Jun. 2007. 17 pages.
Skog, Johan, et al."Glioblastoma microvesicles transport RNA and protein that promote tumor growth and provide diagnostic biomarkers." Nat Cell Biol. Dec. 2008 ; 10(12): 1470-1476. doi:10.1038/ncb1800. 16 pages.
Montecalvo, Angela, et al. "Mechanism of transfer of functional microRNAs between mouse dendritic cells via exosomes." Blood. Jan. 19, 2012; 119(3): 756-766. 20 pages.
Sun, Dongmei, et al. "A Novel Nanoparticle Drug Delivery System: The Anti-inflammatory Activity of Curcumin is Enhanced When Encapsulated in Exosomes." www.moleculartherapy.org, vol. 18, No. 9, 1606-1614, Sep. 2010. 9 pages.
Tian, Yanhua, et al. "A doxorubicin delivery platform using engineered natural membrane vesicle exosomes for targeted tumor therapy." Biomaterials 35 (2014) 2383-2390. 8 pages.
Kamerkar, Sushrut, et al. "Exosomes facilitate therapeutic targeting of oncogenic KRAS in pancreatic cancer." Nature vol. 546, pp. 498-503, Jun. 22, 2017. 24 pages.
Smyth, Tyson, et al. "Surface Functionalization of Exosomes Using Click Chemistry." Bioconjugate Chem. 2014, 25, 1777-1784. 8 pages.
Luan, Xin, et al. "Engineering exosomes as refined biological nanoplatforms for drug delivery." Acta Pharmacologica Sinica (2017) 38: 754-763. 10 pages.
Garcia-Manrique, Pablo, et al. "Fully Artificial Exosomes: Towards New Theranostic Biomaterials." Trends in Biotechnology, Jan. 2018, vol. 36, No. 1. 5 pages.
Li, Yan, et al. "A33 antibody-functionalized exosomes for targeted delivery of doxorubicin against colorectal cancer." Nanomedicine: Nanotechnology, Biology and Medicine, vol. 14, Issue 7, Oct. 2018, pp. 1973-1985. 2 pages.
Hermanson, Greg T. "Preparation of Liposome Conjugates and Derivatives." Bioconjugate Techniques, 2008. 42 pages.
Hermanson, Greg T. "Bioconjugate Techniques." Academic Press 1996. pp. 0-73. 100 pages.
Hermanson, Greg T. "Bioconjugate Techniques." Academic Press 1996. pp. 74-173. 100 pages.
Hermanson, Greg T. "Bioconjugate Techniques." Academic Press 1996. pp. 174-273. 100 pages.
Hermanson, Greg T. "Bioconjugate Techniques." Academic Press 1996. pp. 274-373. 100 pages.
Hermanson, Greg T. "Bioconjugate Techniques." Academic Press 1996. pp. 374-473. 100 pages.
Hermanson, Greg T. "Bioconjugate Techniques." Academic Press 1996. pp. 474-573. 100 pages.
Hermanson, Greg T. "Bioconjugate Techniques." Academic Press 1996. pp. 574-673. 100 pages.
Hermanson, Greg T. "Bioconjugate Techniques." Academic Press 1996. pp. 674-785. 100 pages.
"SNA Platform." exicure. http://www.exicuretx.com/science-technology/sna-platform.php. Last Accessed Nov. 19, 2018. 3 pages.
Mirkin, Ekaterina, et al. "Transcription regulartory elements are punctuation marks for DNA replication." PNAS, vol. 103, No. 19, May 9, 2006. 6 pages.
Dogra, Navneet, et al. "Investigating Ligand-Receptor Interactions at Bilayer Surface Using Electronic Absorption Spectroscopy and Fluorescence Resonance Energy Transfer." Langmuir 2012, 28, 12989-12998. 10 pages.
Sterman, Daniel H., et al. "A Phase I Trial of Repeated Intrapleural Adenoviral-mediated Interferon-β Gene Transfer for Mesothelioma and Metastatic Pleural Effusions." Mol Ther. Apr. 2010; 18(4): 852-860. 9 pages.

* cited by examiner

FUNCTIONALIZING AN EXOSOME BY BONDING A CHEMICALLY MODIFIED MOLECULAR CARGO TO A SURFACE BIOMOLECULE LOCATED ON A BILAYER MEMBRANE OF THE EXOSOME AND OPPOSITE A CYTOPLASM OF THE EXOSOME ← 902

DELIVERING, BY THE EXOSOME, THE CHEMICALLY MODIFIED MOLECULAR CARGO TO A BIOLOGICAL CELL OR TISSUE ← 904

```
┌─────────────────────────────────────────────────────────────┐
│ FUNCTIONALIZING AN EXOSOME BY BONDING A CHEMICALLY          │
│ MODIFIED MOLECULAR CARGO TO A SURFACE BIOMOLECULE           │ ← 1002
│ LOCATED ON A BILAYER MEMBRANE OF THE EXOSOME AND            │
│ OPPOSITE A CYTOPLASM OF THE EXOSOME                         │
└─────────────────────────────────────────────────────────────┘
                              ↓
┌─────────────────────────────────────────────────────────────┐
│ FUNCTIONALIZING THE EXOSOME BY BONDING A SECOND             │
│ CHEMICALLY MODIFIED MOLECULAR CARGO TO A SECOND             │ ← 1004
│ SURFACE BIOMOLECULE LOCATED ON THE BILAYER                  │
│ MEMBRANE AND OPPOSITE THE CYTOPLASM                         │
└─────────────────────────────────────────────────────────────┘
                              ↓
┌─────────────────────────────────────────────────────────────┐
│ DELIVERING, BY THE EXOSOME, THE CHEMICALLY MODIFIED         │ ← 1006
│ MOLECULAR CARGO TO A BIOLOGICAL CELL OR TISSUE              │
└─────────────────────────────────────────────────────────────┘
```

```
┌─────────────────────────────────────────────────────────┐
│ ISOLATING, BY A MOLECULAR PROBE, AN EXOSOME FROM A      │
│ PLURALITY OF EXOSOMES BASED ON A COMPOSITION OF A       │──1102
│ SURFACE BIOMOLECULE LOCATED ON A BILAYER MEMBRANE       │
│ OF THE EXOSOME AND OPPOSITE A CYTOPLASM OF THE          │
│                    EXOSOME                              │
└─────────────────────────────────────────────────────────┘
                            │
                            ▼
┌─────────────────────────────────────────────────────────┐
│                                                         │──1104
│   FUNCTIONALIZING THE SURFACE WITH MOLECULAR CARGO      │
└─────────────────────────────────────────────────────────┘
```

```
┌─────────────────────────────────────────────────────────────┐
│ ISOLATING, BY A MOLECULAR PROBE, AN EXOSOME FROM A          │
│ PLURALITY OF EXOSOMES BASED ON A COMPOSITION OF A           │ ← 1202
│ SURFACE BIOMOLECULE LOCATED ON A BILAYER MEMBRANE           │
│ OF THE EXOSOME AND OPPOSITE A CYTOPLASM OF THE              │
│ EXOSOME                                                     │
└─────────────────────────────────────────────────────────────┘
                              │
                              ▼
┌─────────────────────────────────────────────────────────────┐
│ BONDING A MOLECULAR CARGO TO A SECOND SURFACE               │
│ BIOMOLECULE LOCATED ON THE BILAYER MEMBRANE AND             │ ← 1204
│ OPPOSITE THE CYTOPLASM                                      │
└─────────────────────────────────────────────────────────────┘
                              │
                              ▼
┌─────────────────────────────────────────────────────────────┐
│ DELIVERING, BY THE EXOSOME, THE MOLECULAR CARGO TO A        │
│ BIOLOGICAL CELL, WHEREIN THE EXOSOME HAS A CHEMICAL         │ ← 1206
│ AFFINITY TOWARDS THE BIOLOGICAL CELL                        │
└─────────────────────────────────────────────────────────────┘
```

EXOSOME VESSELS FOR DELIVERY OF MOLECULAR CARGO

BACKGROUND

The subject disclosure relates to one or more exosomes that can facilitate delivery of molecular cargo, and more specifically, to one or more exosomes with functionalized surfaces to transport one or more molecular cargos to desired biological cells and/or tissues.

Three constraints affecting nano-technologies for delivering of molecular cargo to specific cells or tissues include: biocompatibility, molecular cargo loading efficiency, and/or specificity of the delivery system to cells or tissue of interest. For example, to be biocompatible the delivery system must be non-toxic to the recipient organism and/or maintain its integrity in physiological conditions (e.g. stable at pH 7 and/or avoid immune-detection). Additionally, the molecular cargo delivery system should be able to deliver a wide variety of molecules of interest (e.g., DNA for genetic manipulations, RNA for gene silencing, therapeutics, and/or molecule inhibitors).

Conventional molecular cargo delivery systems are composed of a base delivery vessel and protocols for loading the vessel with the molecular cargo. Further, conventional molecular cargo delivery technologies can then be separated into two categories: nanoparticle technologies and lipid vesicle technologies. However, both nanoparticles and liposome vesicle technologies can experience multiple shortcomings with regard to the constraints and/or considerations described above.

Example nanoparticles that can be utilized in conventional molecular cargo delivery systems include: gold, silver, and/or titanium. Indeed, there are established protocols for covalently attaching a variety of functional groups and consequently a variety of biologically active molecules to nanoparticle metals. However, while many nanoparticles are biocompatible, they tend to accumulate in the body over time and can produce toxicity.

Liposomes are synthetic lipid vesicles that can be prepared with various sizes (e.g., ranging from a few tens of nanometers (nm) to about 10-20 microns (µm) in diameter). Furthermore, the shape, size, morphology and function of liposomes can be engineered by varying lipid's chemical/physical structure and composition. Liposomes have been used for chemical compound delivery and other therapeutic purposes. However, biocompatibility remains a concern as liposomes do not mimic precise cellular (e.g., including lipid and proteins) characteristics. Thus, the widespread utility of nano-particles, such as those made from gold, is questionable due to their inherent non-biodegradability; and liposome-based technologies lack certain lipids and/or protein required for interaction with the plasma membrane of target cells and/or tissues.

An additional conventional molecular cargo delivery technology includes the use of exosomes as delivery vessels. However, modern protocols for loading exosomes are inefficient, time dependent, and/or damaging to the exosomes; thereby, substantially inhibiting the functionality of conventional exosome-based molecular cargo delivery technologies. For example, encapsulating nucleic acid sequences in exosomes by electroporation is inefficient (e.g., only a small fraction of the subject exosomes is appropriately loaded with the molecular cargo and/or the process can damage the exosomes). In another example, click chemistry is used to functionalize the surface of exosomes so that molecular cargo can be externally attached. While this process does not suffer from the inefficiencies of electroporation, it requires 24 hours of constant stirring at harsh conditions, which can adversely alter exosome morphology and/or biochemistry. Thus, conventional techniques are not sufficient to efficiently use exosomes to transport cargo.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein molecules and/or methods that can facilitate the transportation and/or delivery of molecular cargo are described.

According to an embodiment, a molecule is provided. The molecule can comprise a chemically modified molecular cargo bonded to a surface biomolecule of an exosome. The surface biomolecule can be located on a bilayer membrane of the exosome opposite a cytoplasm of the exosome. An advantage of such a molecule can be the use of one or more exosomes to delivery one or more therapeutic compounds.

In some examples, the surface biomolecule can be a chemical compound selected from a group consisting of a protein, an antibody, an antigen, a phospholipid, a glycolipid, a nucleic acid, a polysaccharide, a sugar, and a delocalized backbone molecule of the bilayer membrane. An advantage of such a molecule can be that naturally occurring surface structures of exosomes can be utilized to facilitate one or more bioconjugations with molecular cargo.

According to an embodiment, a method is provided. The method can comprise functionalizing an exosome by bonding a chemically modified molecular cargo to a surface biomolecule located on a bilayer membrane of the exosome and opposite a cytoplasm of the exosome. An advantage of such a method can be the formation of one or more exosome vessels to facilitate transportation and/or delivery of one or more molecular cargos. Furthermore, surface biomolecules containing hydrophobic group or carbon chain can also be intercalated within the bilayer membrane scaffold.

In some examples, the method can also comprise functionalizing the exosome by bonding a second chemically modified molecular cargo to a second surface biomolecule located on the bilayer membrane and opposite the cytoplasm. An advantage of such a method can be that the one or more synthesized exosome vessels can be loaded with various types of molecular cargos simultaneous to enhance one or more transportation and/or delivery functions.

According to an embodiment, a method is provided. The method can comprise isolating, by a molecular probe, an exosome from a plurality of exosomes based on a composition of a surface biomolecule located on a bilayer membrane of the exosome and opposite a cytoplasm of the exosome. An advantage of such a method is that specific types of exosomes can be utilized to create one or more exosome vessels for the transportation and/or delivery of molecular cargos.

In some examples, the method can also comprise delivering, by the exosome, the molecular cargo to a biological cell. The exosome can have a chemical affinity towards the biological cell. An advantage of such a method can be the target-specific transportation and/or delivery of molecular cargo by exosomes to biological cells of interest.

BRIEF DESCRIPTION OF THE DRAWINGS

FIG. 9 illustrates a flow diagram of an example, non-limiting method that can facilitate functionalizing one or more exosomes to facilitate transportation and/or delivery of one or more molecular cargos in accordance with one or more embodiments described herein.

FIG. 10 illustrates a flow diagram of an example, non-limiting method that can facilitate functionalizing one or more exosomes to facilitate transportation and/or delivery of one or more molecular cargos in accordance with one or more embodiments described herein.

FIG. 11 illustrates a flow diagram of an example, non-limiting method that can comprise isolating one or more exosomes of interest to facilitate specific delivery functionality of one or more molecular cargos in accordance with one or more embodiments described herein.

FIG. 12 illustrates a flow diagram of an example, non-limiting method that can comprise isolating one or more exosomes of interest to facilitate specific delivery functionality of one or more molecular cargos in accordance with one or more embodiments described herein.

DETAILED DESCRIPTION

Figure 1:
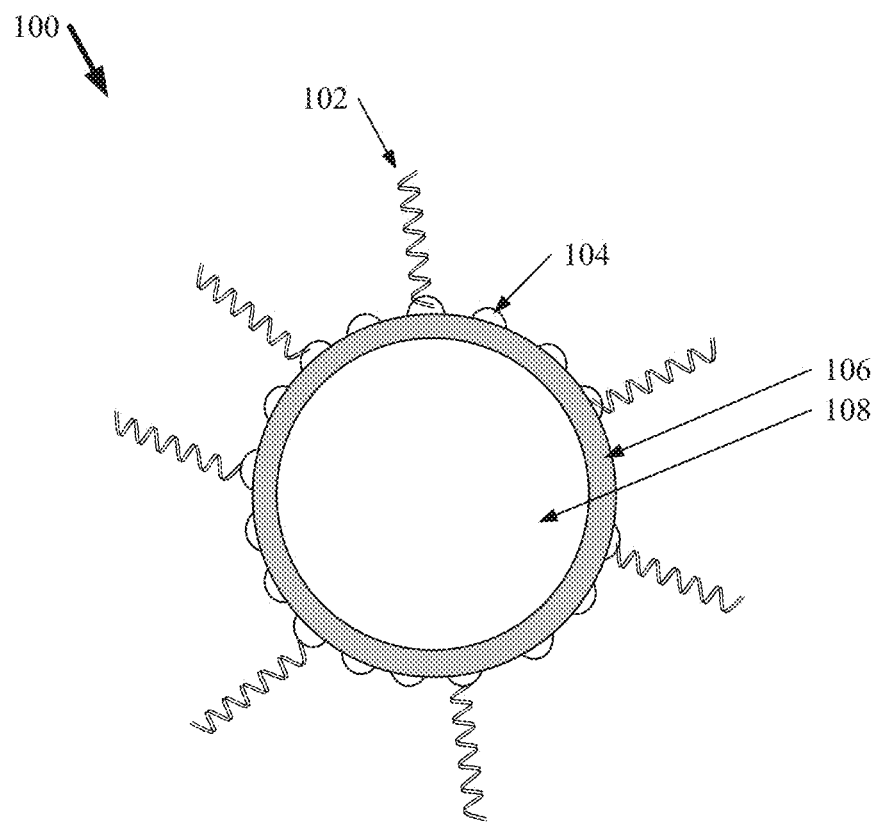
FIG. 1 illustrates a diagram of an example, non-limiting exosome vessel that can have a surface functionalized with one or more molecular cargos in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the above problems with conventional molecular cargo delivery systems; the present disclosure can be implemented to produce a solution to one or more of these problems in the form of one or more molecules and/or methods that can utilize exosomes as vessels to transport and/or deliver molecular cargo. For example, the exosome vessels described herein can satisfy the three constraints for an effective biomolecular delivery system described above. The biocompatibility constraint can be met by isolating naturally secreted exosomes from cells in bodily fluids and/or in cell culture media, which can also maintain the fundamental stability of exosomes under physiological conditions. The loading efficiency constraint can be met by forming covalent bonds between surface biomolecules (e.g., phospholipids, proteins, and/or carbohydrates) that are readily present on the exosome surface with chemically modified molecular cargo (e.g., most reaction steps can be carried out on the biomolecules, which bind on the exosomes surface to avoid harsh reaction conditions on exosomes). Further, one or more exosome vessels can achieve specificity towards target biological cells and/or tissues by covalently attaching specific antibodies to the exosome surface. Being proteins themselves, the antibodies can be functionalized to react with biomolecules other than proteins.

Various embodiments described herein can regard functionalized exosome vessels and/or methods to facilitate the transportation and/or delivery of molecular cargo. For example, one or more embodiments described herein can comprise conjugating one or more molecular cargos (e.g., nucleic acids and/or proteins) to one or more biomolecules located on the surface of one or more exosomes; thereby loading the one or more molecular cargos to the exosome vessel for transportation and/or delivery to one or more desired biological cells and/or tissues. In one or more embodiments, the conjugation can be established by one or more covalent bonds between the one or more molecular cargos and the one or more surface biomolecules. Further, by conjugating one or more antibodies and/or antigens to the one or more surface biomolecules of an exosome, the subject exosome can be a vessel with a chemical affinity to specific, target biological cells and/or tissues.

FIG. 1 illustrates diagram of an example, non-limiting exosome vessel 100 functionalized with one or more molecular cargos 102. For example, FIG. 1 depicts an exemplary exosome vessel 100 comprising one or more nucleic acid molecular cargos 102 conjugated to one or more surface biomolecules 104 of the exosome vessel 100 (e.g., wherein the wavy lines shown in FIG. 1 can represent the one or more nucleic acids).

As used herein, the term "exosome" can refer to a small (e.g., having a diameter of 30 to 200 nm) vesicle of endocytic origin that can be secreted through fusion of multi-vesicular bodies and/or a plasma membrane to an extracellular environment. Exosomes can comprise a diversity of biomolecules, including, but not limited to: transmembrane proteins, cytosolic proteins, enzymes, surface proteins, nucleic acids, lipids, a combination thereof and/or the like. As shown in FIG. 1, exosomes can comprise a bilayer membrane 106 defining a cytoplasm 108 interior of the exosome. One of ordinary skill in the art will readily recognize that the bilayer membrane 106 can comprise phospholipid bilayers and/or the cytoplasm 108 can house various features of the subject exosome (e.g., enzymes, proteins, nucleic acids, a combination thereof, and/or the like). Exosomes can be transported throughout a biological body by one or more diverse bodily fluids, such as: saliva, urine, blood, serum, plasma, sweat, tears, a combination thereof, and/or the like. In various embodiments, the one or more exosome vessels 100 described herein can be exosomes with one or more molecular cargos 102 conjugated to a surface of the bilayer membrane 106 (e.g., via one or more naturally residing surface structure).

The one or more exosome vessels 100 can comprise one or more surface biomolecules 104. The one or more surface biomolecules 104 can be located on a surface of the bilayer membrane 106 and/or at least partially within the bilayer membrane 106. For instance, the one or more surface biomolecules 104 can be located on the bilayer membrane 106 opposite the cytoplasm 108 (e.g., located outside the interior of the one or more exosome vessels 100). Example surface biomolecules 104 can include, but are not limited to: proteins, antibodies, antigens, phospholipids, glycolipids, nucleic acids, polysaccharides, sugars, carbohydrates, enzymes, exosomal bilayer membrane 106 scaffolds, a combination thereof, and/or the like.

Further, the one or more surface biomolecules 104 can comprise one or more target functional groups, which can facilitate conjugation with the one or more molecular cargos 102. Example target functional groups that can be comprised within the one or more surface biomolecules 104 can include, but are not limited to: primary amines (e.g., lysine groups, arginine groups, a combination thereof, and/or the like), cysteine groups, phosphate groups, hydroxyl groups, carboxy groups, a combination thereof, and/or the like. In one or more embodiments, the one or more target functional groups can establish a covalent bond with the one or more molecular cargos 102 to facilitate conjugation of the one or more molecular cargos 102 to the surface of the exosome vessel 100. The exosome vessel 100 can comprise a variety of different types of surface biomolecules 104 on and/or within the bilayer membrane 106. Further, the number of surface biomolecules 104 depicted in FIG. 1 is exemplary, and one of ordinary skill in the art will recognize that the one or more exosome vessels 100 can comprise fewer or additional surface biomolecules 104 than the seventeen shown in FIG. 1.

One or more molecular cargos 102 can be radially arranged on the surface of the exosome vessel 100 through chemical interaction with the one or more surface biomolecules 104 and/or can comprise one or more nucleic acids (e.g., as shown in FIG. 1) and/or one or more proteins (e.g., antibodies and/or antigens). For example, one or more of the molecular cargos 102 can be one or more therapeutic chemical compounds defined by one or more nucleic acids. The one or more exosome vessels 100 can transport and/or deliver the one or more therapeutic chemical compounds to one or more target biological cells and/or tissues. Additionally, one or more of the molecular cargos 102 can be one or more can be antibodies and/or antigens, which can functionalize the one or more exosome vessels 100 with a chemical affinity towards specific biological cells and/or tissues. In one or more embodiments, the one or more exosome vessels 100 can comprise a mixture of various types of molecular cargos 102.

Figure 2:
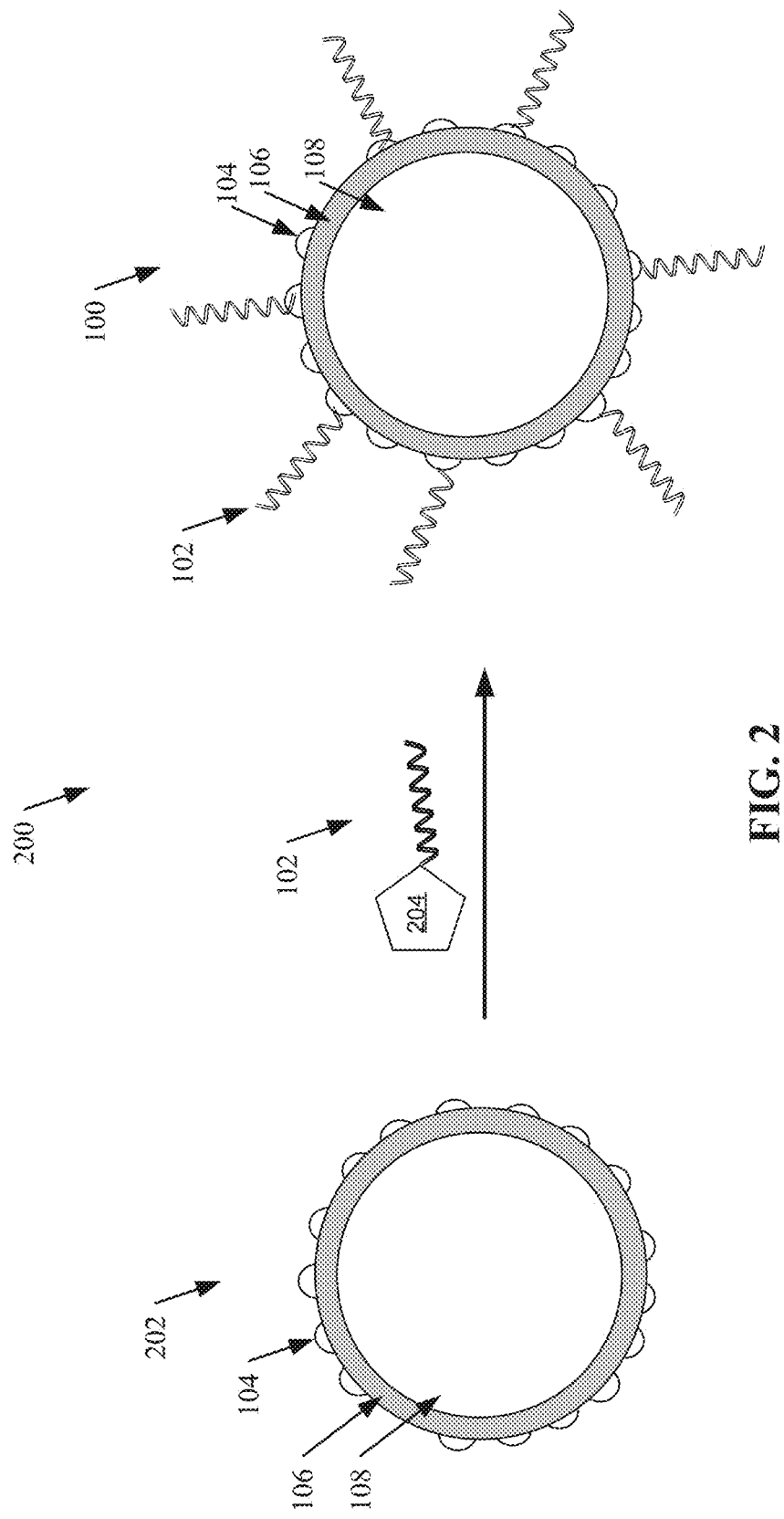
FIG. 2 illustrates a diagram of an example, non-limiting functionalization process that can facilitate forming an exosome vessel, which can transport and/or deliver one or more molecular cargos in accordance with one or more embodiments described herein.

FIG. 2 illustrates a diagram of an example, non-limiting first conjugation scheme 200 that can facilitate conjugation of the one or more molecular cargos 102 to the one or more surface biomolecules in accordance with one or more embodiments described herein. Repetitive description of like elements employed in other embodiments described herein is omitted for sake of brevity. As shown in FIG. 2, the exemplary first conjugation scheme 200 can comprise conjugating an initial exosome 202 with one or more molecular cargos 102 to form one or more exosome vessels 100. In one or more embodiments, the one or more molecular cargos 102 and/or the one or more initial exosomes 202 can be mixed together in a basic solution (e.g., having a pH of greater than or equal to 7 and less than or equal to 10) to facilitate the first conjugation scheme 200.

The one or more initial exosomes 202 can comprise the one or more surface biomolecules 104 that can be targeted for conjugation by the one or more molecular cargos 102. Further, the one or more molecular cargos 102 (e.g., comprising nucleic acids, as shown in FIG. 2, and/or one or more proteins, such as antibodies and/or antigens) can comprise one or more reactive functional groups 204. The one or more reactive functional groups 204 can chemically interact with the one or more functional groups of the one or more surface biomolecules 104 to establish a covalent bond between the one or molecule cargos 102 and the one or more surface biomolecules 104.

Example chemical compounds that can comprise the one or more reactive functional groups 204 can include, but are not limited to: amine-reactive compounds, phosphate-reactive compounds, hydroxyl-reactive compounds, carboxyl-reactive compounds, antibodies, antigens, a combination thereof, and/or the like. Amine-reactive compounds can include any reactive groups capable of reacting with an amine to form a covalent bond. Example amine-reactive compounds can include, but are not limited to: an N-hydroxysuccinimide ("NHS") ester, a sulfo-N-hydroxysuccinimide ester, an imidoester, a fluorophenyl ester, an epoxide, an isothiocyanate, an isocyanate, a sulfonyl chloride, an aldehyde, a carbodiimide, an acyl azide, an anhydride, a fluorobenzene, a carbonate, a combination thereof, and/or the like. For instance, the one or more functional groups can couple with one or more side chains of an amino acid, such as the primary amines of arginine and/or lysine. Phosphate-reactive compounds can include any reactive groups capable of reacting with a phosphate group to form a covalent bond. Example, phosphate-reactive compounds can include, but are not limited to: carbodiimide, alkyl groups, aryl groups, acyl groups, a combination thereof, and/or the like. Hydroxyl-reactive compounds can include any reactive groups capable of reacting with a hydroxyl group to form a covalent bond. Example hydroxyl-reactive compounds can include, but are not limited to: alkyl groups, aryl groups, acyl groups, a combination thereof, and/or the like. Carboxyl-reactive compounds can include any reactive groups capable of reacting with an carboxyl to form a covalent bond.

In various embodiments, the one or more exosome vessels 100 can transport nucleic acids (e.g., synthetic nucleic acids) to enable a variety of therapeutic functions. For example, the one or more nucleic acids comprised within the one or more molecular cargos 102 can be immune-stimulatory oligonucleotides, which can activate one or more immune signaling networks innate to a biological cell and/or tissue interacting the one or more exosome vessels 100. For example, the one or more molecular cargos 102 can comprise synthetic nucleic acids that can: initiate antigen presentation and/or co-stimulation, activate innate immune cells (e.g., macrophages and/or dendritic cells, induce production of pro-inflammatory cytokines, a combination thereof, and/or the like. In another example, the one or more molecular cargos 102 transported and/or delivered by the one or more exosome vessels 100 can comprise synthetic nucleic acids, which can perform one or more therapeutic techniques within a subject biological cell and/or tissue, including, but not limited to: antisense techniques, ribonucleic acid ("RNA") interference techniques, splice-switching techniques, messenger RNA-based therapeutics, a combination thereof, and/or the like.

In one or more embodiments, one or more antibodies and/or antigens can be used as the one or more reactive functional groups 204. For example, one or more molecular cargos 102 can comprise one or more nucleic acids bonded to one or more antibodies, wherein the one or more antibodies can establish one or more antibody-antigen interactions with one or more surface antigens (e.g., serving as one or more surface biomolecules 104 as described herein) located on the initial exosome 202 to facilitate conjugation of the one or more molecular cargos 102. In another example, one or more molecular cargos 102 can comprise one or more nucleic acids bonded to one or more antigens, wherein the one or more antigens can establish one or more antigen-antibody interactions with one or more surface antibodies (e.g., serving as one or more surface biomolecules 104 as described herein) located on the initial exosome 202 to facilitate conjugation of the one or more molecular cargos 102.

Figure 3:
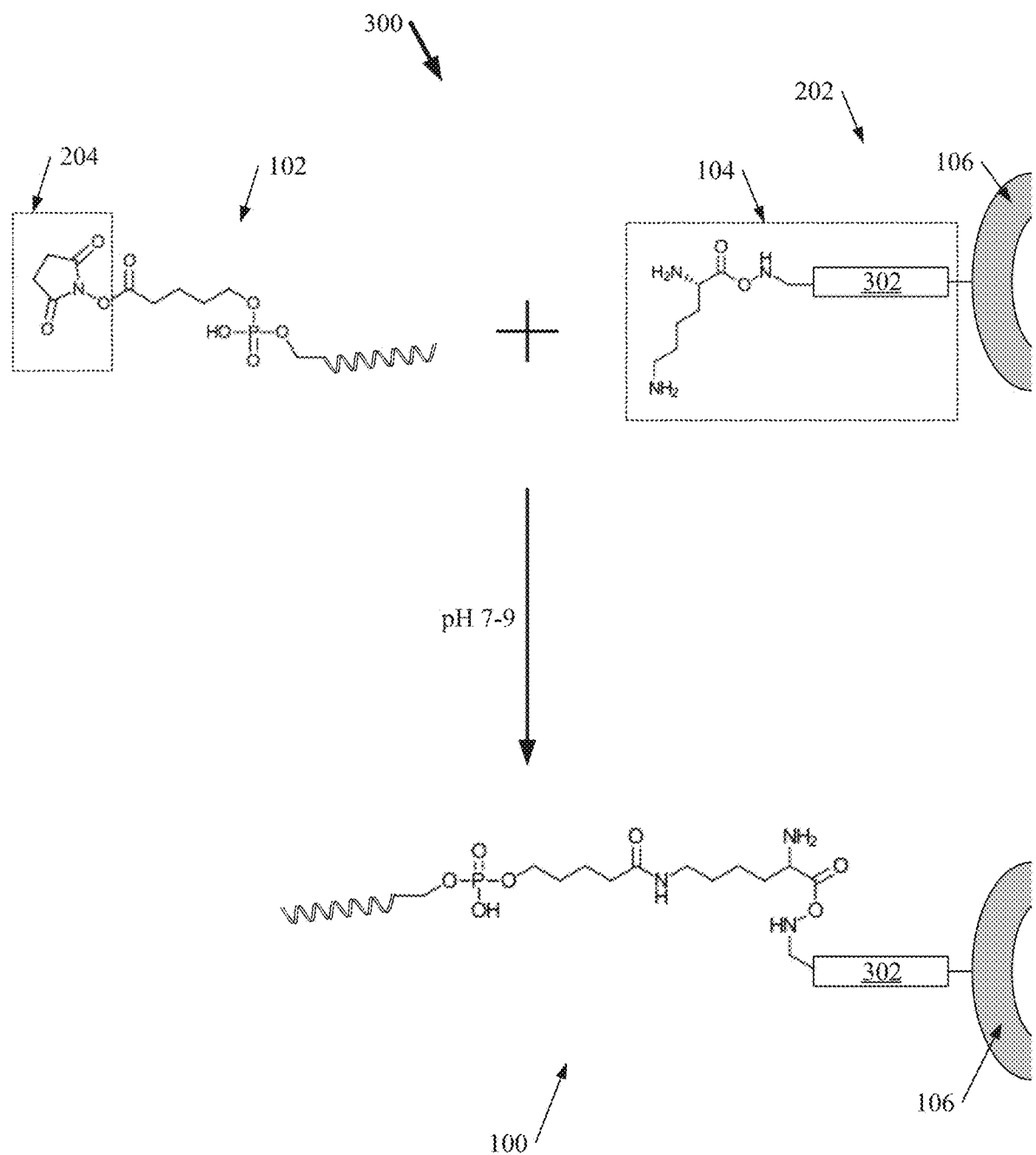
FIG. 3 illustrates a diagram of an example, non-limiting ligand modification that can facilitate attaching one or more molecular cargos to a surface of an exosome in accordance with one or more embodiments described herein.

FIG. 3 illustrates a diagram of an example, non-limiting bioconjugation scheme 300 that can conjugate the one or more molecular cargos 102 to the one or more surface biomolecules 104 (e.g., as described with regards to the first conjugation scheme 200) in accordance with one or more embodiments described herein. Repetitive description of like elements employed in other embodiments described herein is omitted for sake of brevity.

A wide variety of bioconjugation reactions can be utilized to facilitate conjugation of the one or more molecular cargos 102 and the one or more surface biomolecules 104; such as, for example: alkylations, acylations, disulfide bonding, antibody-antigen interactions, amine bonding, phosphate bonding, nucleic acid annealing, a combination thereof, and/or the like. In various embodiments, one or more reactive functional groups 204 of the one or more molecular cargos 102 can react with the one or more target functional groups of the one or more surface biomolecules 104 to establish the bioconjugation reactions.

For instance, bioconjugation scheme 300 depicts an exemplary bioconjugation reaction, wherein the reactive functional group 204 can be an amine-reactive compound and the target functional group of the one or more surface biomolecules 104 can be a primary amino group. FIG. 3 depicts an exemplary molecular cargo 102 structure in accordance with the various embodiments described herein. For example, the exemplary molecular cargo 102 shown in FIG. 3 can comprise one or more nucleic acids (e.g., represented by one or more wavy lines) bonded to an NHS reactive functional group 204. As shown in FIG. 3, the reactive functional group 204 (e.g., a NHS ester) can be bonded to the five-prime ("5'") end of the one or more nucleic acids. Additionally, FIG. 3 depicts an exemplary surface biomolecule 104 structure in accordance with the various embodiments described herein. The exemplary surface biomolecule 104 shown in FIG. 3 can be a protein comprising a polypeptide chain 302 attached to an amine (e.g., lysine, as depicted in FIG. 3). As shown in FIG. 3, the one or more target functional groups can be located at a distal end of the one or more surface biomolecules 104.

In the exemplary bioconjugation scheme 300, the one or more nucleic acid containing molecular cargos 102 can be introduced to the one or more surface biomolecules 104 of an initial exosome 202 in an environment having a pH greater than or equal to 7 and less than or equal to 9. The chemical affinity of the one or more reactive functional groups 204 can facilitate the formation of a covalent bond between the one or more reactive functional groups 204 and the one or more target functional groups. For example, the one or more molecular cargos 102 can covalently bond to a primary amino group comprised within the lysine structure of the one or more protein surface biomolecules 104. As shown in FIG. 3, the resulting bioconjugation can render the one or more nucleic acids of the molecular cargo 102 bonded to the one or more surface biomolecules 104 (e.g., the one or more proteins on the surface of the initial exosome 202); thereby forming an exosome vessel 100 that can transport and/or delivery the one or more bonded nucleic acids.

While FIG. 3 depicts exemplary structures for the one or more molecular cargos 102 and/or the one or more surface biomolecules 104, the architecture of the bioconjugations described herein is not so limited. For example, the one or more reactive functional groups 204 and/or the one or more target functional groups can comprise any chemical structures supported by the various chemical categories and/or examples described herein. Additionally, while FIG. 3 depicts a bioconjugation of one or more nucleic acids with one or more proteins, the architecture of the bioconjugations described herein is not so limited. For example, as described herein, the one or more molecular cargos 102 can comprise one or more proteins (e.g., antibodies and/or antigens) and/or the one or more surface biomolecules can be antibodies, antigens, phospholipids, glycolipids, nucleic acids, polysaccharides, sugars, carbohydrates, exosomal bilayer membrane 106 scaffolds, a combination thereof, and/or the like.

Figure 4:
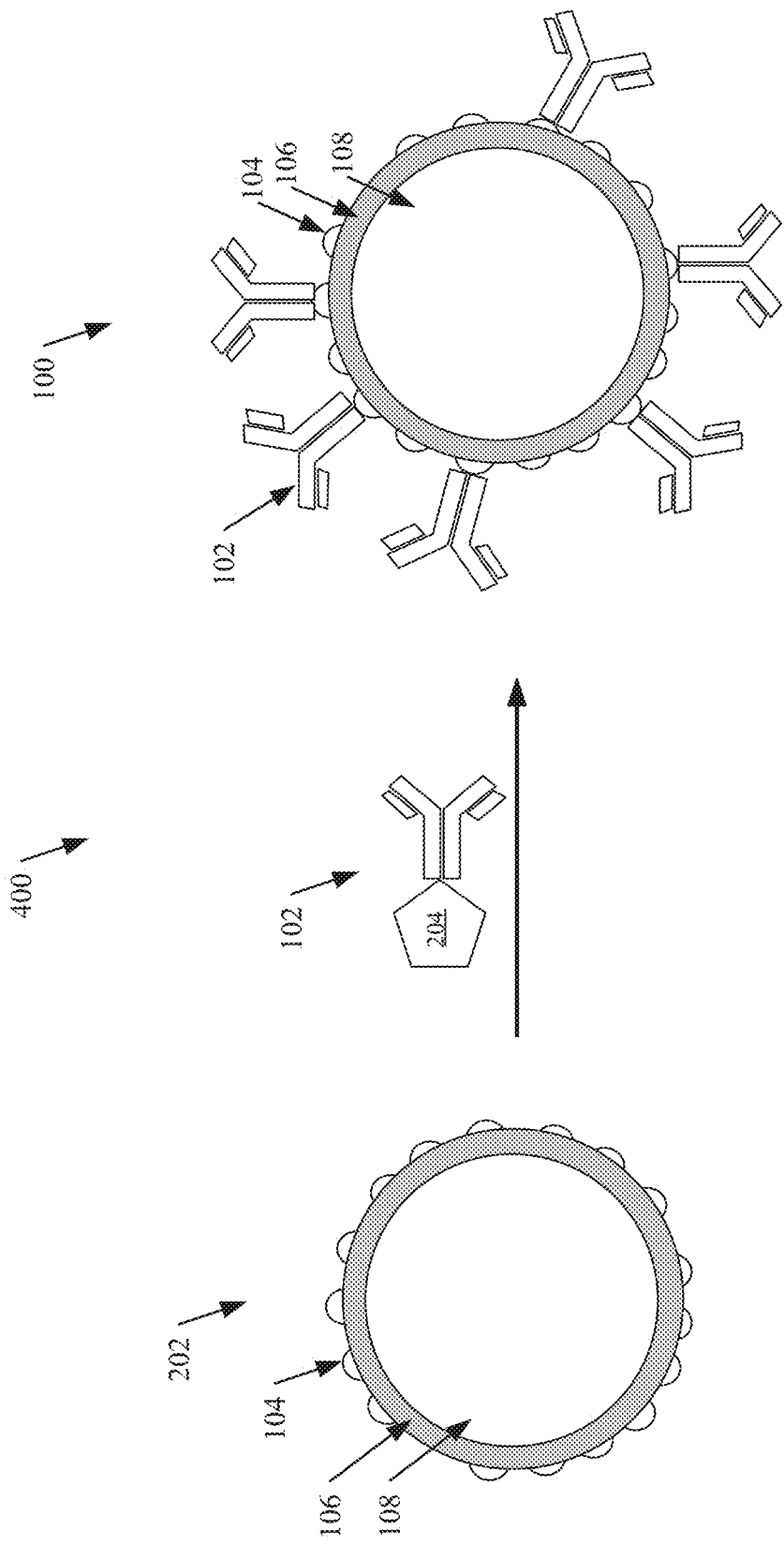
FIG. 4 illustrates a diagram of an example, non-limiting functionalization process that can facilitate forming an exosome vessel, which can transport and/or deliver one or more molecular cargos in accordance with one or more embodiments described herein.

FIG. 4 illustrates a diagram of an example, non-limiting second conjugation scheme 400 that can facilitate conjugation of the one or more molecular cargos 102 to the one or more surface biomolecules 104 in accordance with one or more embodiments described herein. Repetitive description of like elements employed in other embodiments described herein is omitted for sake of brevity. As shown in FIG. 4, the exemplary second conjugation scheme 400 can comprise conjugating an initial exosome 202 with one or more molecular cargos 102 to form one or more exosome vessels 100. In one or more embodiments, the one or more molecular cargos 102 and/or the one or more initial exosomes 202 can be mixed together in a basic solution (e.g., having a pH of greater than or equal to 7 and less than or equal to 9) to facilitate the second conjugation scheme 400.

The second conjugation scheme 400 can exemplify that the one or more molecular cargos 102 can comprise one or more antibodies (e.g., depicted as "Y"-shaped structures in FIG. 4) bonded to the one or more reactive functional groups 204. As described herein with regards to FIGS. 2 and/or 3, the one or more reactive functional groups 204 can facilitate bonding the one or more antibodies of the one or more molecular cargos 102 to the one or more surface biomolecules 104 of the initial exosome 202. By bonding the one or more antibodies to the surface of the exosome vessel 100, the exosome vessel 100 can be functionalized to target specific biological cells and/or tissues. For example, one or more exosome vessels 100 carrying molecular cargo 102 containing antibodies (e.g., as shown in FIG. 4) can be chemically attracted to one or more biological cells and/or tissues comprising the type of antigen that can bond to the antibodies. In other words, antibody molecular cargo 102 (e.g., as shown in FIG. 4) can enable antibody-antigen interactions between the one or more exosome vessels 100 and one or more target biological cells and/or tissues; thereby adding specificity to the transportation and/or delivery functionality of the one or more exosome vessels 100. Additionally, in one or more embodiments, the one or more molecular cargos 102 can comprise one or more antigens (not shown) to enable antibody-antigen interactions between the one or more exosome vessels 100 and one or more target biological cells and/or tissues comprising specific antibodies.

Figure 5:
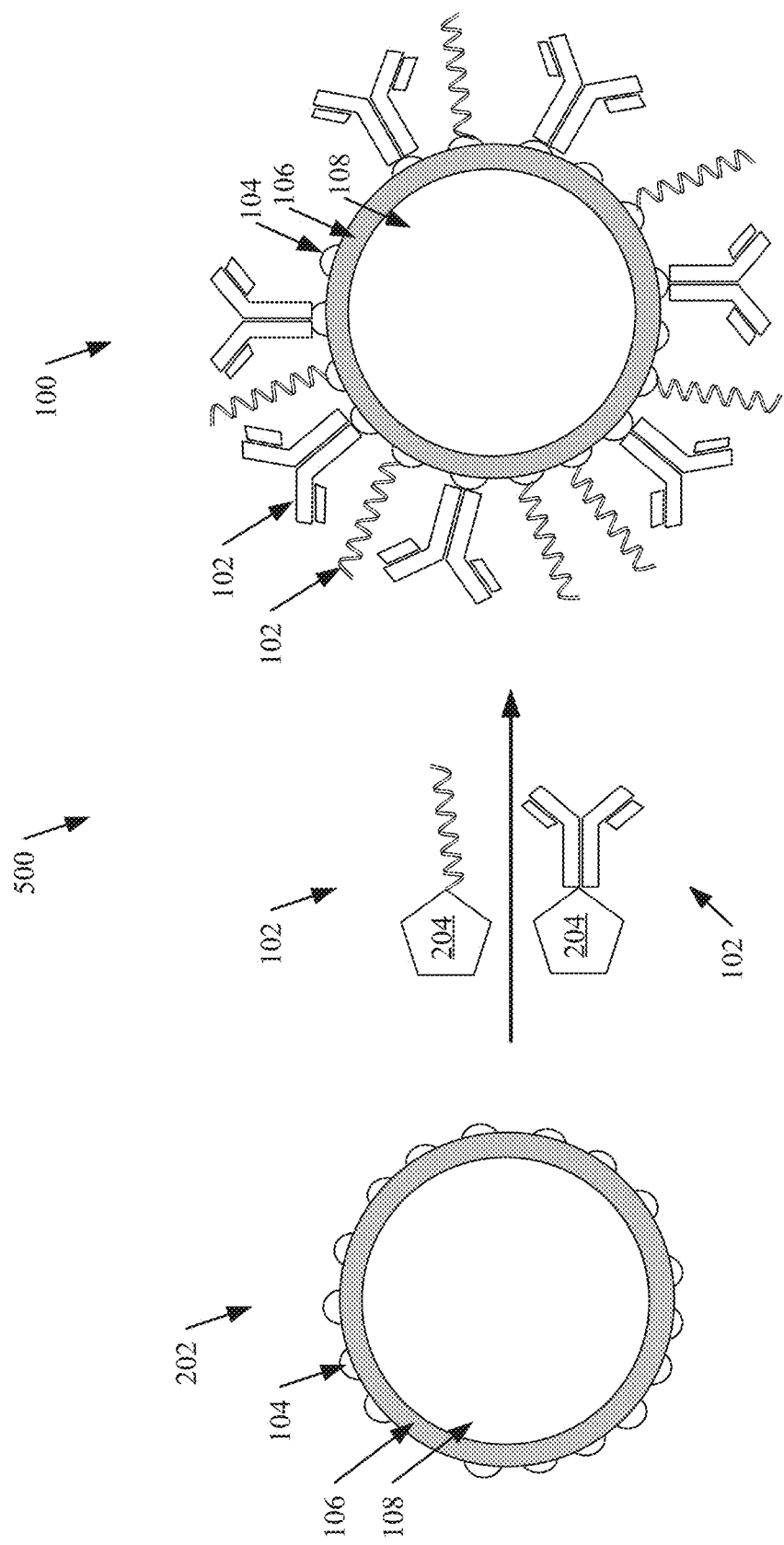
FIG. 5 illustrates a diagram of an example, non-limiting functionalization process that can facilitate forming an exosome vessel, which can transport and/or deliver one or more molecular cargos in accordance with one or more embodiments described herein.

FIG. 5 illustrates a diagram of an example, non-limiting third conjugation scheme 500 that can facilitate conjugation of the one or more molecular cargos 102 to the one or more surface biomolecules 104 in accordance with one or more embodiments described herein. Repetitive description of like elements employed in other embodiments described herein is omitted for sake of brevity. As shown in FIG. 5, the exemplary third conjugation scheme 500 can comprise conjugating an initial exosome 202 with multiple molecular cargos 102 to form one or more exosome vessels 100. In one or more embodiments, the one or more molecular cargos 102 and/or the one or more initial exosomes 202 can be mixed together in a basic solution (e.g., having a pH of greater than or equal to 7 and less than or equal to 9) to facilitate the second conjugation scheme 400.

The third conjugation scheme 500 exemplifies that the one or more exosome vessels 100 can comprise a plurality of different types of molecular cargos 102. For example, FIG. 5 depicts an example exosome vessel 100 comprising a first type of molecular cargo 102 comprising one or more nucleic acids and a second type of molecular cargo 102 comprising one or more antibodies (e.g., the one or more wavy lines can represent nucleic acids and/or the one or more "Y"-shaped structures can represent antibodies). As shown in the third conjugation scheme 500, the various types of molecular cargos 102 can be conjugated to the one or more initial exosomes 202 simultaneously. For example, molecular cargos 102 comprising nucleic acids and molecular cargos 102 comprising antibodies can be conjugated to the one or more initial exosomes 202 at the same time. Alternatively, one or more first type of molecular cargos 102 (e.g., comprising one or more nucleic acids) can be conjugated with the one or more initial exosomes 202, whereupon the resulting exosome vessel 100 can be further conjugated with one or more second type of molecular cargos 102 (e.g., comprising one or more antibodies).

The conjugation of a variety of different types of molecular cargos 102 can enhance the functionality of the one or more exosome vessels 100. For example, as described herein, conjugating one or more nucleic acid molecular cargos 102 can enable the one or more exosome vessels 100 to transport and/or delivery therapeutic chemical compounds. Further, conjugating protein (e.g., antibody and/or antigen) molecular cargos 102 to the subject exosome vessels 100 can incorporate specificity to the transportation and/or delivery of the therapeutic chemical compounds. Thus, one or more exosome vessels 100 conjugated with both nucleic acid molecular cargos 102 and protein (e.g., antibody and/or antigen) molecular cargos 102 can advantageously transport and/or deliver therapeutic chemical compounds to target biological cells and/or tissues.

Figure 6:
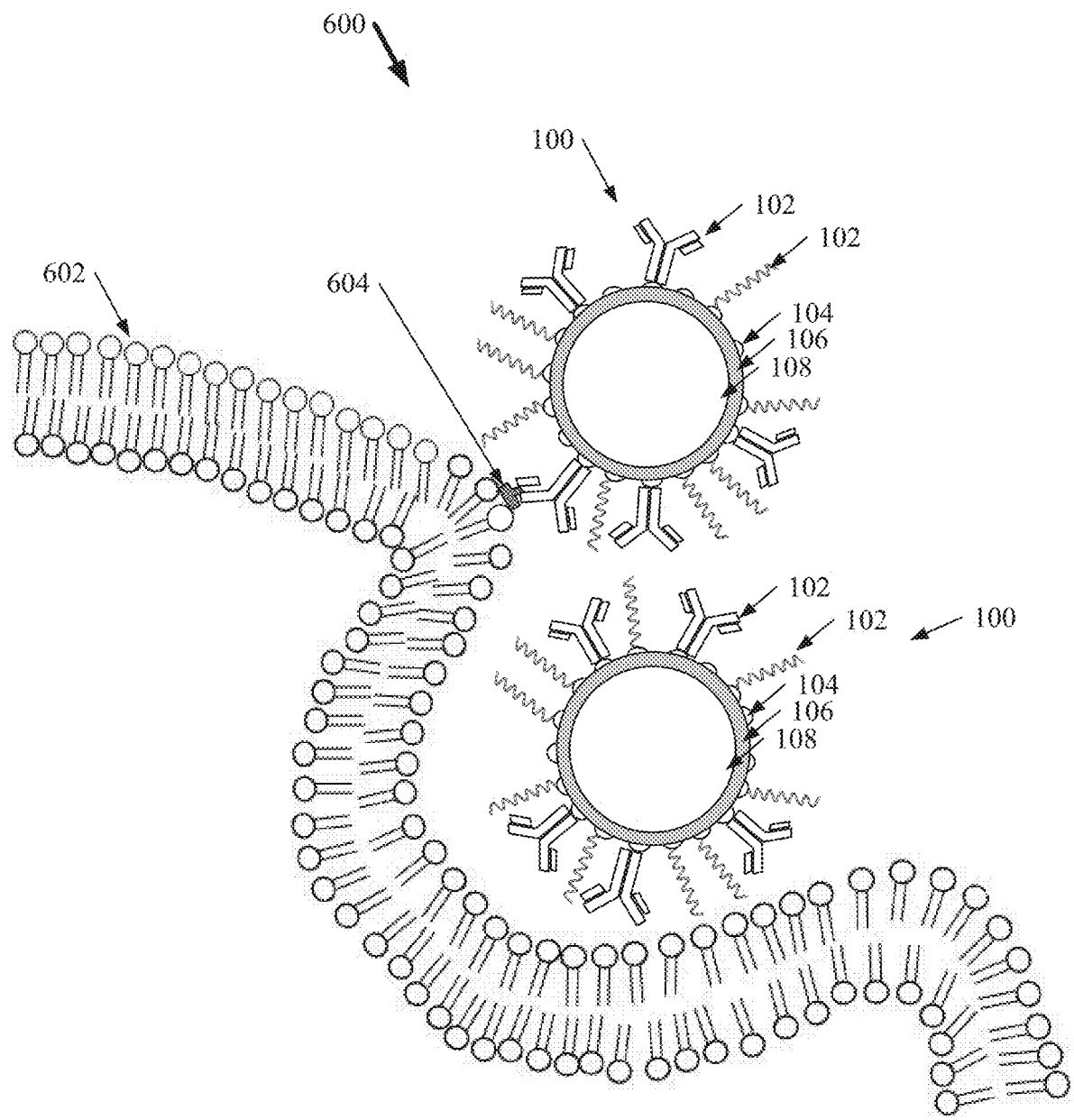
FIG. 6 illustrates a diagram of an example, non-limiting delivery process that can comprise one or more exosome vessels transporting one or more molecular cargos to a plasma membrane of target biological cells and/or tissues in accordance with one or more embodiments described herein.

FIG. 6 illustrates a diagram of an example, non-limiting delivery process 600 that can be facilitate by the one or more exosome vessels 100 in accordance with one or more embodiments described herein. Repetitive description of like elements employed in other embodiments described herein is omitted for sake of brevity. As shown in FIG. 6, the one or more exosome vessels 100 can transport one or more molecular cargos 102 to the plasma membrane 602 of one or more biological cells and/or tissues.

For example, the one or more exosome vessels 100 can transport the one or more molecular cargos 102 across the plasma membrane 602. In one or more embodiments, the one or more exosome vessels 100 can adhere to the plasma membrane 602 via one or more interactions between one or more surface biomolecules 104 and/or one or more cellular receptors positioned on and/or within the plasma membrane 602. In addition, in various embodiments the one or more exosome vessels 100 can be attracted to and/or otherwise adhere to the plasma membrane 602 due to an antibody-antigen interaction between the one or more surface biomolecules 104 and one or more target antigens 604 located on the plasma membrane 602. For example, the one or more exosome vessels 100 can comprise one or more molecular cargos 102 comprising proteins (e.g., antibodies and/or antigens) with a chemical affinity towards the plasma membrane 602 (e.g., towards a target antigen 604 and/or target antibody located on the surface of the plasma membrane 602). Once adhered to the plasma membrane 602, the one or more exosome vessels 100 can: elicit transduction of soluble signaling via intracellular signaling pathways; fuse with the plasma membrane 602, thereby transferring the one or more molecular cargos 102 across the plasma membrane 602; and/or be endocytosed via phagocytosis, micropinocytosis, receptor-mediated endocytosis, and/or raft-mediated endocytosis. For instance, in one or more embodiments the one or more exosome vessels 100 can be internalized into one or more biological cells and/or tissues by receptor-mediated endocytosis, wherein one or more ligands (e.g., surface biomolecules 104 and/or molecular cargos 102) located on the surface of the exosome vessel 100 (e.g., located on the bilayer membrane 106) can engage one or more cell receptors (e.g., scavenger receptors) located on the plasma membrane 602. Furthermore, the one or more exosome vessels 100 can be internalized through one or more endocytosis mechanisms.

Figure 7:
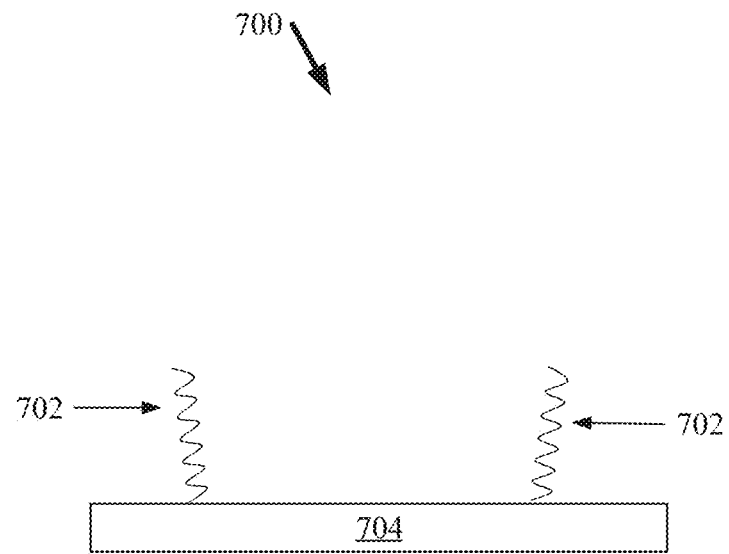
FIG. 7 illustrates a diagram of an example, non-limiting on-chip probe that can facilitate isolating one or more exosomes of interest in accordance with one or more embodiments described herein.

FIG. 7 illustrates a diagram of an example, non-limiting on-chip probe 700 that can be utilized to isolate one or more initial exosomes 202 from a plurality of exosome samples in accordance with one or more embodiments described herein. Repetitive description of like elements employed in other embodiments described herein is omitted for sake of brevity. As shown in FIG. 7, the one or more on-chip probes 700 can comprise one or more molecular probes 702 (e.g., delineated by dashed lines in FIG. 7) attached to a substrate 704. The one or more molecular probes 702 can be single stranded nucleic acid complexes (e.g., represented as wavy lines in FIG. 7), which can be complementary to one or more single strand nucleic acids bonded onto a surface of the bilayer membrane 106 of one or more initial exosomes 202.

As shown in FIG. 7, the one or more molecular probes 702 can be fixed to one or more substrates 704. Example materials that can comprise the one or more substrates 704 can include, but are not limited to: silicon, polydimethylsiloxane ("PDMS"), poly(methyl methacrylate) ("PMMA"), a combination thereof, and/or the like. In one or more embodiments, the one or more molecular probes 702 can be fixed to the one or more substrates 704 by physical adsorption, thiol, amines, nucleic acid-biotin, a combination thereof, and/or the like.

Figure 8:
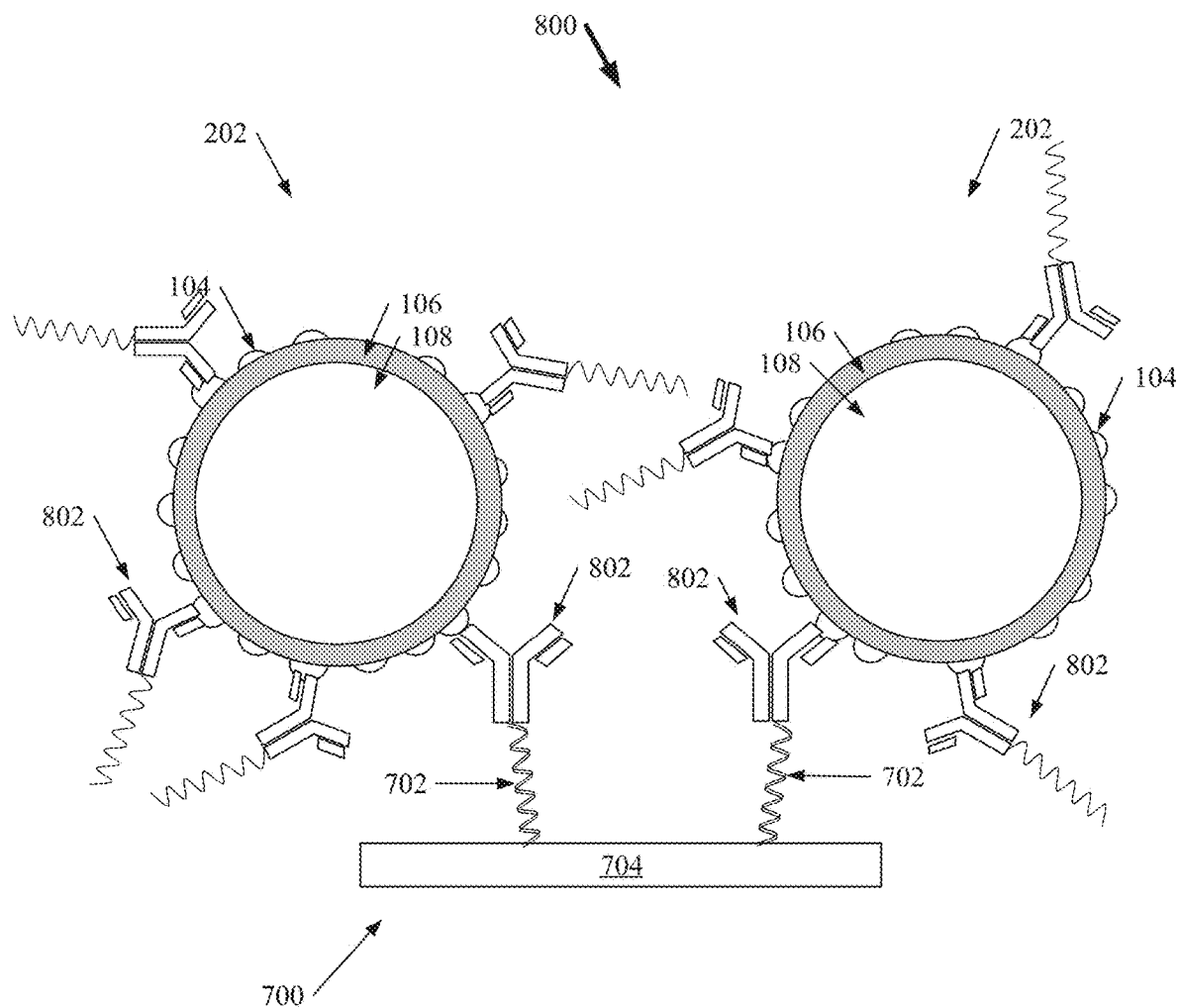
FIG. 8 illustrates a diagram of an example, non-limiting isolation process that can capture one or more exosomes of interest for specific delivery functionality of one or more molecular cargos in accordance with one or more embodiments described herein.

FIG. 8 illustrates a diagram of an example, non-limiting exosome isolation process 800 that can be performed to isolate one or more initial exosomes 202 from a plurality of exosome samples in accordance with one or more embodiments described herein. Repetitive description of like elements employed in other embodiments described herein is omitted for sake of brevity. As shown in FIG. 8, the exosome isolation process 800 can utilize the one or more on-chip probes 700 to collect one or more initial exosomes 202 of interest.

A sample comprising a plurality of exosomes can be introduced (e.g., by a lithographic technique, submerging in desired solution, or a microfluidic system) to the one or more on-chip probes 700. As the one or more plurality of exosomes pass the one or more on-chip probes 700, one or more chemical compounds on the surface of the exosomes can be attracted to and/or otherwise interact with the one or more molecular probes 702 secured to the one or more substrates 704. Exosomes not having one or more surface compounds with a chemical affinity for the one or more molecular probes 702 can pass by the one or more on-chip probes 700 without interaction. In contrast, exosomes comprising one or more surface compounds with a chemical affinity for the molecular probes 702 can chemically interact (e.g., anneal) with, and/or thereby be captured by, the one or more molecular probes 702. Thus, the exosome isolation process 800 can isolate exosomes with specific surface compositions based on the selection of chemical compounds comprising the one or more molecular probes 702 (e.g., the one or more second portions 708).

For instance, the surface of the one or more initial exosomes 202 can be engineered with one or more proteins (e.g., antibodies and/or antigens) comprising a single stranded nucleic acid that is complementary to the one or more molecular probes 702. For example, a nucleic acid-antibody complex 802 can be synthesized comprising a first portion bonded to a second portion. The first portion of the nucleic acid-antibody complex 802 can be a single stranded nucleic acid that is complementary to the single stranded nucleic acid molecular probe 702. The second portion of the nucleic acid-antibody complex 802 can be one or more antibodies with an affinity to bond to one or more surface biomolecules 104 of the initial exosomes 202 of interest. For example, the one or more antibodies can have an affinity to bond to one or more antigen surface biomolecules 104 (e.g., have an affinity to initiate an antibody-antigen interaction with one or more surface biomolecules 104 located on the initial exosomes 202 of interest). Thus, the one or more nucleic acid-antibody complexes 802 can functionalize the surface of target initial exosomes 202 with single stranded nucleic acid that is complementary to the one or more molecular probes 702. As shown in FIG. 8, the one or more nucleic acid-antibody complexes 802 can further anneal with the one or more molecular probes 702, thereby the on-chip probe 700 can capture one or more initial exosomes 202 of interest (e.g., one or more initial exosomes 202 comprising specific surface biomolecules 104, such as specific antigens that can assist in transportation specificity by the one or more exosome vessels 100)

While FIG. 8 depicts an on-chip probe 700 comprising a plurality of molecular probes 702 having the same, or substantially the same, chemical structure; the architecture of the molecular probes 702 is not so limited. For example, in one or more embodiments one or more of the molecular probes 702 comprised within an on-chip probe 700 can have a different structure than one or more other molecular probes 702 comprised within the on-chip probe 700. For example, a first molecular probe 702 can comprise a first single strand nucleic acid sequence while a second molecular probe 702 can comprise a different single strand nucleic acid sequence. An on-chip probe 700 comprising a plurality of molecular probes 702 with two or more different structures can isolate two or more different types of target exosomes via the exosome isolation process 800.

In one or more embodiments, exosomes isolated by the exosome isolation process 800 can serve as initial exosomes 202 for the one or more bioconjugation reactions described herein to form the one or more exosome vessels 100. For example, the exosome isolation process 800 can be utilized to conjugate one or more molecular cargos 102 to initial exosomes 202 with specific surface structures (e.g., specific compositions of surface biomolecules 104) to enhance and/or enable one or more features of the delivery process 600. For instance, wherein it can be advantageous for the delivery process 600 to target one or more specific biological cells and/or tissues, the exosome isolation process 800 can isolate initial exosomes 202 having one or more surface biomolecules 104 having a chemical affinity towards one or more biomolecules of the biological cells and/or tissues of interest; thereby facilitating transportation and/or delivery of the one or more molecular cargos 102 to specific biological cells and/or tissues. In another instance, the one or more surface biomolecules 104 targeted by the exosome isolation process 800 can enhance and/or enable uptake of the one or more molecular cargos 102 by the one or more target biological cells and/or tissues (e.g., enhance and/or enable one or more endocytosis processes, such as phagocytosis, micropinocytosis, receptor-mediated endocytosis, and/or raft-mediated endocytosis.

FIG. 9 illustrates a flow diagram of an example, non-limiting method 900 that can facilitate transporting and/or delivering one or more molecular cargos 102 using one or more exosome vessels 100 in accordance with one or more embodiments described herein. Repetitive description of like elements employed in other embodiments described herein is omitted for sake of brevity.

At 902, the method 900 can comprise functionalizing one or more exosomes (e.g., one or more initial exosomes 202) by bonding one or more chemically modified molecular cargos 102 to one or more surface biomolecules 104 located on a bilayer membrane 106 of the one or more exosomes and opposite a cytoplasm 108 of the one or more exosomes. For example, the functionalizing can be performed in accordance with the first conjugation scheme 200, the second conjugation scheme 400, and/or the third conjugation scheme 500 described herein. For instance, the one or more molecular cargos 102 can comprise one or more nucleic acids and/or proteins (e.g., antibodies and/or antigens) and/or one or more reactive functional groups 204 (e.g., amine-reactive compounds, phosphate-reactive compounds, hydroxyl-reactive compounds, antibodies, and/or antigens). Further, the one or more surface biomolecules 104 can comprise one or more functional groups that can facilitate a chemical interaction (e.g., covalent bonding and/or antibody-antigen interactions) with the one or more reactive functional groups 204. Example surface biomolecules 104 can include: proteins (e.g., antibodies and/or antigens), phospholipids, glycolipids, nucleic acids, polysaccharides, sugars, delocalized backbone molecules of the bilayer membrane 106, enzymes, a combination thereof, and/or the like.

As a result of the functionalization, the one or more molecular cargos 102 can be bonded to the surface of the one or more initial exosomes 202 in a radial arrangement to form one or more exosome vessels 100.

At 904, the method 900 can comprise delivering, by the exosome, the one or more chemically modified molecular cargo 102 to one or more biological cells and/or tissues. For example, the delivering at 904 can be performed in accordance with the delivery process 600 described herein. In one or more embodiments, the one or more chemically modified molecular cargos 102 bonded to the one or more exosomes (e.g., bonded to the one or more initial exosomes 202) can enable the one or more exosome vessels 100 to target one or more specific biological cells and/or tissues for delivery of the one or more molecular cargos 102. For example, one or more of the molecular cargos 102 can comprise one or more antibodies that can be specifically attracted to one or more antigens of one or more biological cells and/or tissues of interest. Further the one or more exosome vessels 100 can deliver the one or more molecular cargos 102 by: eliciting transduction of soluble signaling via intracellular signaling pathways; fusion with the plasma membrane 602 of the one or more biological cells and/or tissues, thereby transferring the one or more molecular cargos 102 across the plasma membrane 602; and/or endocytosis via phagocytosis, micropinocytosis, receptor-mediated endocytosis, and/or raft-mediated endocytosis. For instance, in one or more embodiments the one or more exosome vessels 100 can be internalized into one or more biological cells and/or tissues by receptor-mediated endocytosis, wherein one or more ligands (e.g., surface biomolecules 104 and/or molecular cargos 102) located on the surface of the exosome vessel 100 (e.g., located on the bilayer membrane 106) can engage one or more cell receptors (e.g., scavenger receptors) located on the plasma membrane 602. Delivery of the one or more molecular cargos 102 can facilitate one or more therapeutic therapies, such as: antisense techniques, ribonucleic acid ("RNA") interference techniques, splice-switching techniques, messenger RNA-based therapeutics, microRNA-based therapeutics, a combination thereof, and/or the like.

FIG. 10 illustrates a flow diagram of an example, non-limiting method 1000 that can facilitate transporting and/or delivering one or more molecular cargos 102 using one or more exosome vessels 100 in accordance with one or more embodiments described herein. Repetitive description of like elements employed in other embodiments described herein is omitted for sake of brevity.

At 1002, the method 1000 can comprise functionalizing one or more exosomes (e.g., one or more initial exosomes 202) by bonding one or more chemically modified molecular cargos 102 to one or more surface biomolecules 104 located on a bilayer membrane 106 of the one or more exosomes and opposite a cytoplasm 108 of the one or more exosomes. For example, the functionalizing can be performed in accordance with the first conjugation scheme 200, the second conjugation scheme 400, and/or the third conjugation scheme 500 described herein. For instance, the one or more chemically modified molecular cargos 102 can comprise one or more nucleic acids and/or proteins (e.g., antibodies and/or antigens) and/or one or more reactive functional groups 204 (e.g., amine-reactive compounds, phosphate-reactive compounds, hydroxyl-reactive compounds, antibodies, and/or antigens). Further, the one or more surface biomolecules 104 can comprise one or more functional groups that can facilitate a chemical interaction (e.g., covalent bonding and/or antibody-antigen interactions) with the one or more reactive functional groups 204. Example surface biomolecules 104 can include, but are not limited to: proteins (e.g., antibodies and/or antigens), phospholipids, glycolipids, nucleic acids, polysaccharides, sugars, delocalized backbone molecules of the bilayer membrane 106, enzymes, a combination thereof, and/or the like. As a result of the functionalization, the one or more molecular cargos 102 can be bonded to the surface of the one or more initial exosomes 202 in a radial arrangement to form one or more exosome vessels 100.

At 1004, the method 1000 can comprise functionalizing the one or more exosomes by bonding one or more second chemically modified molecular cargos 102 to one or more second surface biomolecules 104 located on the bilayer membrane 106 and opposite the cytoplasm 108. For example, the functionalizing at 1004 can be performed in accordance with the third conjugation scheme 500 described herein. For instance, the one or more second chemically modified molecular cargos 102 can comprise one or more nucleic acids and/or proteins (e.g., antibodies and/or antigens) and/or one or more reactive functional groups 204 (e.g., amine-reactive compounds, phosphate-reactive compounds, hydroxyl-reactive compounds, antibodies, and/or antigens). The one or more reactive functional groups 204 of the one or more second chemically modified molecular cargos 102 can facilitate one or more bonds (e.g., bioconjugation reactions, covalent bonding, and/or antibody-antigen interactions) with the one or more second surface biomolecules 104. In one or more embodiments, the one or more chemically modified molecular cargos 102 and the one or more second chemically modified molecular cargos 102 can have different chemical compositions so as to impart different functionalities to the one or more exosome vessels 100. For example, the one or more chemically modified molecular cargos 102 and the one or more second chemically modified molecular cargos 102 can be bonded to the one or more initial exosomes 202 via one or more bioconjugation reactions simultaneously and/or sequentially (e.g., the bioconjugation of the one or more chemically modified molecular cargos 102 can be performed without substantially inhibiting the bioconjugation of the one or more second chemically modified molecular cargos 102). By functionalizing the one or more exosomes (e.g., one or more initial exosomes 202) with a plurality of different chemically modified molecular cargos 102, the one or more resulting exosome vessels 100 can exhibit multiple functionalities (e.g., therapeutic functionality, and target-specific delivery).

At 1006, the method 1000 can comprise delivering, by the exosome, the one or more chemically modified molecular cargo 102 to one or more biological cells and/or tissues. For example, the delivering at 1006 can be performed in accordance with the delivery process 600 described herein. In one or more embodiments, the one or more chemically modified molecular cargos 102 bonded to the one or more exosomes (e.g., bonded to the one or more initial exosomes 202) can enable the one or more exosome vessels 100 to target one or more specific biological cells and/or tissues for delivery of the one or more molecular cargos 102. For example, one or more of the molecular cargos 102 can comprise one or more antibodies that can be specifically attracted to one or more antigens of one or more biological cells and/or tissues of interest. Further the one or more exosome vessels 100 can delivery the one or more molecular cargos 102 by: eliciting transduction of soluble signaling via intracellular signaling pathways; fusion with the plasma membrane 602 of the one or more biological cells and/or tissues, thereby transferring the one or more molecular cargos 102 across the plasma membrane 602; and/or endocytosis via phagocytosis, micropinocytosis, receptor-mediated endocytosis, and/or raft-mediated endocytosis. For instance, in one or more embodiments the one or more exosome vessels 100 can be internalized into one or more biological cells and/or tissues by receptor-mediated endocytosis, wherein one or more ligands (e.g., surface biomolecules 104 and/or molecular cargos 102) located on the surface of the exosome vessel 100 (e.g., located on the bilayer membrane 106) can engage one or more cell receptors (e.g., scavenger receptors) located on the plasma membrane 602. Delivery of the one or more molecular cargos 102 can facilitate one or more therapeutic therapies, such as: antisense techniques, ribonucleic acid ("RNA") interference techniques, splice-switching techniques, messenger RNA-based therapeutics, microRNA-based therapeutics, a combination thereof, and/or the like.

FIG. 11 illustrates a flow diagram of an example, non-limiting method 1100 that can facilitate transporting and/or delivering one or more molecular cargos 102 using one or more exosome vessels 100 in accordance with one or more embodiments described herein. Repetitive description of like elements employed in other embodiments described herein is omitted for sake of brevity.

At 1102, the method 1100 can comprise isolating, by one or more molecular probes 702, one or more exosomes from a plurality of exosomes based on a composition of one or more surface biomolecules 104 located on a bilayer membrane 106 of the one or more exosomes and opposite a cytoplasm 108 of the one or more exosomes. For example, the isolating at 1102 can be performed in accordance with the exosome isolation process 800 described herein. In one or more embodiments, the one or more molecular probes 702 can be comprised within one or more on-chip probes 700, wherein the one or more molecular probes 702 can be fixed to one or more substrates 704. Further, the one or more molecular probes 702 can comprise a first portion 706 (e.g., comprising one or more nucleic acids) bonded to the one or more substrates 704 and/or a second portion 708 (e.g., comprising one or more antibodies and/or antigens) of the one or more molecular probes 702. The second portion 708 can chemically interact (e.g., via one or more bioconjugations and/or antibody-antigen interactions) with the one or more surface biomolecules 104 on the surface of the exosomes. The chemical compounds comprising the second portion 708 can have a chemical affinity to bond and/or otherwise interact with specific chemical compounds; thereby exosomes isolated by the one or more molecular probes 702 can be exosomes comprising the one or more specific chemical compounds (e.g., in accordance with the bioconjugation reactions and/or antibody-antigen interactions described herein). For example, the second portion 708 can comprise one or more antibodies and/or one or more exosomes comprising one or more antigens targeted by the one or more antibodies can be captured by the one or molecular probes 702 and thereby subject to isolation. In various embodiments, the on-chip probe 700 can comprise a plurality of molecular probes 702 with comprising different chemical compounds to isolate a plurality of exosomes have different surface compositions.

At 1104, the method 1100 can comprise functionalizing the surface with one or more molecular cargos 102. For example, the functionalizing can be performed in accordance with the first conjugation scheme 200, the second conjugation scheme 400, and/or the third conjugation scheme 500 described herein. For instance, the one or more molecular cargos 102 can comprise one or more nucleic acids and/or proteins (e.g., antibodies and/or antigens) and/ or one or more reactive functional groups 204 (e.g., amine-reactive compounds, phosphate-reactive compounds, hydroxyl-reactive compounds, antibodies, and/or antigens). As a result of the functionalization, the one or more molecular cargos 102 can be bonded to the surface of the one or more initial exosomes 202 in a radial arrangement to form one or more exosome vessels 100.

FIG. 12 illustrates a flow diagram of an example, non-limiting method 1200 that can facilitate transporting and/or delivering one or more molecular cargos 102 using one or more exosome vessels 100 in accordance with one or more embodiments described herein. Repetitive description of like elements employed in other embodiments described herein is omitted for sake of brevity.

At 1202, the method 1200 can comprise isolating, by one or more molecular probes 702, one or more exosomes from a plurality of exosomes based on a composition of one or more surface biomolecules 104 located on a bilayer membrane 106 of the one or more exosomes and opposite a cytoplasm 108 of the one or more exosomes. For example, the isolating at 1102 can be performed in accordance with the exosome isolation process 800 described herein. In one or more embodiments, the one or more molecular probes 702 can be comprised within one or more on-chip probes 700, wherein the one or more molecular probes 702 can be fixed to one or more substrates 704. Further, the one or more molecular probes 702 can comprise a first portion 706 (e.g., comprising one or more nucleic acids) bonded to the one or more substrates 704 and/or a second portion 708 (e.g., comprising one or more antibodies and/or antigens) of the one or more molecular probes 702. The second portion 708 can chemically interact (e.g., via one or more bioconjugations and/or antibody-antigen interactions) with the one or more surface biomolecules 104 on the surface of the exosomes. The chemical compounds comprising the second portion 708 can have a chemical affinity to bond and/or otherwise interact with specific chemical compounds; thereby exosomes isolated by the one or more molecular probes 702 can be exosomes comprising the one or more specific chemical compounds (e.g., in accordance with the bioconjugation reactions and/or antibody-antigen interactions described herein). For example, the second portion 708 can comprise one or more antibodies and/or one or more exosomes comprising one or more antigens targeted by the one or more antibodies can be captured by the one or molecular probes 702 and thereby subject to isolation. In various embodiments, the on-chip probe 700 can comprise a plurality of molecular probes 702 with comprising different chemical compounds to isolate a plurality of exosomes have different surface compositions.

At 1204, the method 1200 can comprise bonding one or more molecular cargos 102 to one or more second surface biomolecules 104 located on the bilayer membrane 106 and opposite the cytoplasm 108. For example, the bonding at 1204 can be performed in accordance with the first conjugation scheme 200, the bioconjugation scheme 300, the second conjugation scheme 400, and/or the third conjugation scheme 500 described herein. For instance, the one or more molecular cargos 102 can comprise one or more nucleic acids and/or proteins (e.g., antibodies and/or antigens) and/or one or more reactive functional groups 204 (e.g., amine-reactive compounds, phosphate-reactive compounds, hydroxyl-reactive compounds, antibodies, and/or antigens). Further, the one or more second surface biomolecules 104 can comprise one or more functional groups that can facilitate a chemical interaction (e.g., covalent bonding and/or antibody-antigen interactions) with the one or more reactive functional groups 204. Example second surface biomolecules 104 can include, but are not limited to: proteins (e.g., antibodies and/or antigens), phospholipids, glycolipids, nucleic acids, polysaccharides, sugars, delocalized backbone molecules of the bilayer membrane 106, enzymes, a combination thereof, and/or the like. As a result of the bonding, the one or more molecular cargos 102 can be bonded to the surface of the one or more isolated exosomes in a radial arrangement to form one or more exosome vessels 100.

At 1206, the method 1200 can comprise delivering, by the one or more exosomes (e.g., one or more exosome vessels 100), the one or more molecular cargo 102 to one or more biological cells and/or tissues, wherein the one or more exosomes can have a chemical affinity towards to the one or more biological cells and/or tissues. For example, the delivering at 1206 can be performed in accordance with the delivery process 600 described herein. In one or more embodiments, the one or more molecular cargos 102 bonded to the one or more isolated exosomes (e.g., bonded to the one or more initial exosomes 202) can enable the one or more exosome vessels 100 to target one or more specific biological cells and/or tissues for delivery of the one or more molecular cargos 102. For example, the one or more exosomes can be isolated at 1202 based on their chemical affinity towards the one or more biological cells and/or tissues (e.g., the same surface biomolecules 104 that can facilitate one or more chemical interactions with the one or more molecular probes 702 can also facilitate one or more chemical interactions with the one or more biological cells and/or tissues). Further the one or more exosome vessels 100 can deliver the one or more molecular cargos 102 by: eliciting transduction of soluble signaling via intracellular signaling pathways; fusion with the plasma membrane 602 of the one or more biological cells and/or tissues, thereby transferring the one or more molecular cargos 102 across the plasma membrane 602; and/or endocytosis via phagocytosis, micropinocytosis, receptor-mediated endocytosis, and/or raft-mediated endocytosis. For instance, in one or more embodiments the one or more exosome vessels 100 can be internalized into one or more biological cells and/or tissues by receptor-mediated endocytosis, wherein one or more ligands (e.g., surface biomolecules 104 and/or molecular cargos 102) located on the surface of the exosome vessel 100 (e.g., located on the bilayer membrane 106) can engage one or more cell receptors (e.g., scavenger receptors) located on the plasma membrane 602 of the one or more biological cells and/or tissues. Delivery of the one or more molecular cargos 102 can facilitate one or more therapeutic therapies, such as: antisense techniques, ribonucleic acid ("RNA") interference techniques, splice-switching techniques, messenger RNA-based therapeutics, microRNA-based therapeutics, a combination thereof, and/or the like.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A dual functionalized exosome, comprising:
    a synthetic nucleic acid bonded to a polypeptide chain of a first surface biomolecule of an exosome,
    wherein the first surface biomolecule is located at an external surface of a bilayer membrane of the exosome opposite a cytoplasm of the exosome,
    wherein the synthetic nucleic acid is bonded to a first functional group, the polypeptide chain of the first surface biomolecule is bonded to a second functional group, and the first functional group and the second functional group are coupled to one another to establish the bonding of the synthetic nucleic acid to the polypeptide chain of the first surface biomolecule, and
    wherein one of the first functional group or the second functional group comprises an antibody or an antigen, and the other of the first functional group or the second functional group comprises the other of the antibody or the antigen; and
    another antibody bonded to a polypeptide chain of a second surface biomolecule of the exosome, and
    wherein the other antibody has a chemical affinity to bond to a biological cell via an antibody-antigen interaction external to the bilayer membrane of the exosome.

2. The dual functionalized exosome of claim 1, in combination with a biological cell or tissue cell in which the dual functionalized exosome is internalized,
    wherein plural ligands at one or more surfaces of the dual functionalized exosome are engaged with one or more cell receptors of a plasma membrane of the biological cell or tissue cell.

3. A method, comprising:
    dually functionalizing an exosome, wherein the dual functionalization comprises
        bonding a synthetic nucleic acid to a first polypeptide chain of a first surface biomolecule,
        wherein the first surface biomolecule is located at an external surface of a bilayer membrane of the exosome opposite a cytoplasm of the exosome, and
        bonding an antibody to a second polypeptide chain of a second surface biomolecule of the exosome, and wherein the antibody has a chemical affinity to bond to a biological cell via an antibody-antigen interaction external to the bilayer membrane of the exosome.

4. The method of claim 3,
wherein the bonding of the synthetic nucleic acid to the first polypeptide chain is established by a bioconjugation reaction between a reactive functional group bonded to the synthetic nucleic acid and a target functional group comprised within the first surface biomolecule and coupled to the first polypeptide chain of the first surface biomolecule,
wherein the reactive functional group comprises a first chemical compound selected from a first group consisting of an amine-reactive compound, a phosphate-reactive compound, a carbodiimide compound, a hydroxyl-reactive compound, and a carboxyl-reactive compound, and
wherein the target functional group comprises a second chemical compound selected from a second group consisting of a primary amine group, a phosphate group, and a hydroxyl group.

5. The method of claim 3,
wherein the bonding of the synthetic nucleic acid is established by a bioconjugation reaction between a reactive functional group bonded to the synthetic nucleic acid and a target functional group comprised within or at the first surface biomolecule and coupled to the first polypeptide chain of the first surface biomolecule,
wherein one of the reactive functional group or the target functional group comprises another antibody or an antigen,
wherein the other of the reactive functional group or the target functional group comprises the other of the other antibody or the antigen, and
wherein the bonding of the synthetic nucleic acid is facilitated by an antibody-antigen interaction between the reactive functional group and the target functional group.

6. The method of claim 3, further comprising:
internalizing the exosome in a biological cell or tissue cell,
wherein plural ligands at one or more surfaces of the exosome are engaged with one or more cell receptors of a plasma membrane of the biological cell or tissue cell.

7. A dual functionalized exosome, comprising:
a synthetic nucleic acid bonded to a first polypeptide chain of a first surface biomolecule of an exosome,
wherein the first surface biomolecule is located at an external surface of a bilayer membrane of the exosome opposite a cytoplasm of the exosome,
wherein, to establish the bonding of the synthetic nucleic acid to the first polypeptide chain, the synthetic nucleic acid is bonded to a first functional group that is coupled to a second functional group of the first surface biomolecule, which second functional group is coupled to the first polypeptide chain,
wherein the first functional group comprises a compound selected from a group consisting of an amine-reactive compound, a phosphate-reactive compound, a carbodiimide compound, and a hydroxyl-reactive compound, and
wherein the second functional group comprises another compound selected from a second group consisting of a primary amine, a phosphate group, and a hydroxyl group; and
an antibody bonded to a second polypeptide chain of a second surface biomolecule of the exosome, and
wherein the antibody has a chemical affinity to bond to a biological cell via an antibody-antigen interaction external to the bilayer membrane of the exosome.

8. The dual functionalized exosome of claim 7, wherein the first surface biomolecule comprises a protein that comprises the first polypeptide chain and the first functional group.

9. The dual functionalized exosome of claim 7, in combination with a biological cell or tissue cell in which the dual functionalized exosome is internalized,
wherein plural ligands at one or more surfaces of the dual functionalized exosome are engaged with one or more cell receptors of a plasma membrane of the biological cell or tissue cell.

* * * * *